(12) United States Patent
Wenner

(10) Patent No.: US 6,635,834 B1
(45) Date of Patent: Oct. 21, 2003

(54) SYSTEM AND METHOD TO DELAY CLOSURE OF A NORMALLY CLOSED ELECTRICAL CIRCUIT

(76) Inventor: Justin Bernard Wenner, 12227 Everglade St., Los Angeles, CA (US) 90066

( * ) Notice: Subject to any disclaimer, the term of this patent is extended or adjusted under 35 U.S.C. 154(b) by 0 days.

(21) Appl. No.: 09/955,610

(22) Filed: Sep. 19, 2001

(51) Int. Cl.⁷ .............................................. H01H 26/00
(52) U.S. Cl. ................ 200/61.08; 200/52 R; 200/61.04
(58) Field of Search ........................... 200/52 R, 61.03, 200/61.04, 61.08, 506, 300, 61.06

(56) References Cited

U.S. PATENT DOCUMENTS 3,997,886 A * 12/1976 Lerner .................... 200/61.04
4,313,042 A * 1/1982 Ehrhart .................... 200/61.04
5,846,744 A * 12/1998 Athey et al. ................. 435/7.9
6,330,465 B1 * 12/2001 Huyberechts et al. ....... 600/343

* cited by examiner

Primary Examiner—Michael Friedhofer
(74) Attorney, Agent, or Firm—Edward J. Chalfie

(57) ABSTRACT

A system and method are provided to delay closure of an electrical circuit of a battery-powered electrical device, intended to operate remotely in an environment in which the pH value changes from one value to another. More specifically, two electrical contacts, at least one being movable, of a normally closed electrical circuit, connecting a battery in series with a battery-powered electrical device, are separated by a material that holds the circuit open until the device is exposed to an environment having a specified pH value. Exposure of the material to an environment having that specified pH value causes the material to dissolve. The dissolving of the material causes the circuit to close, energizing the device.

6 Claims, 2 Drawing Sheets

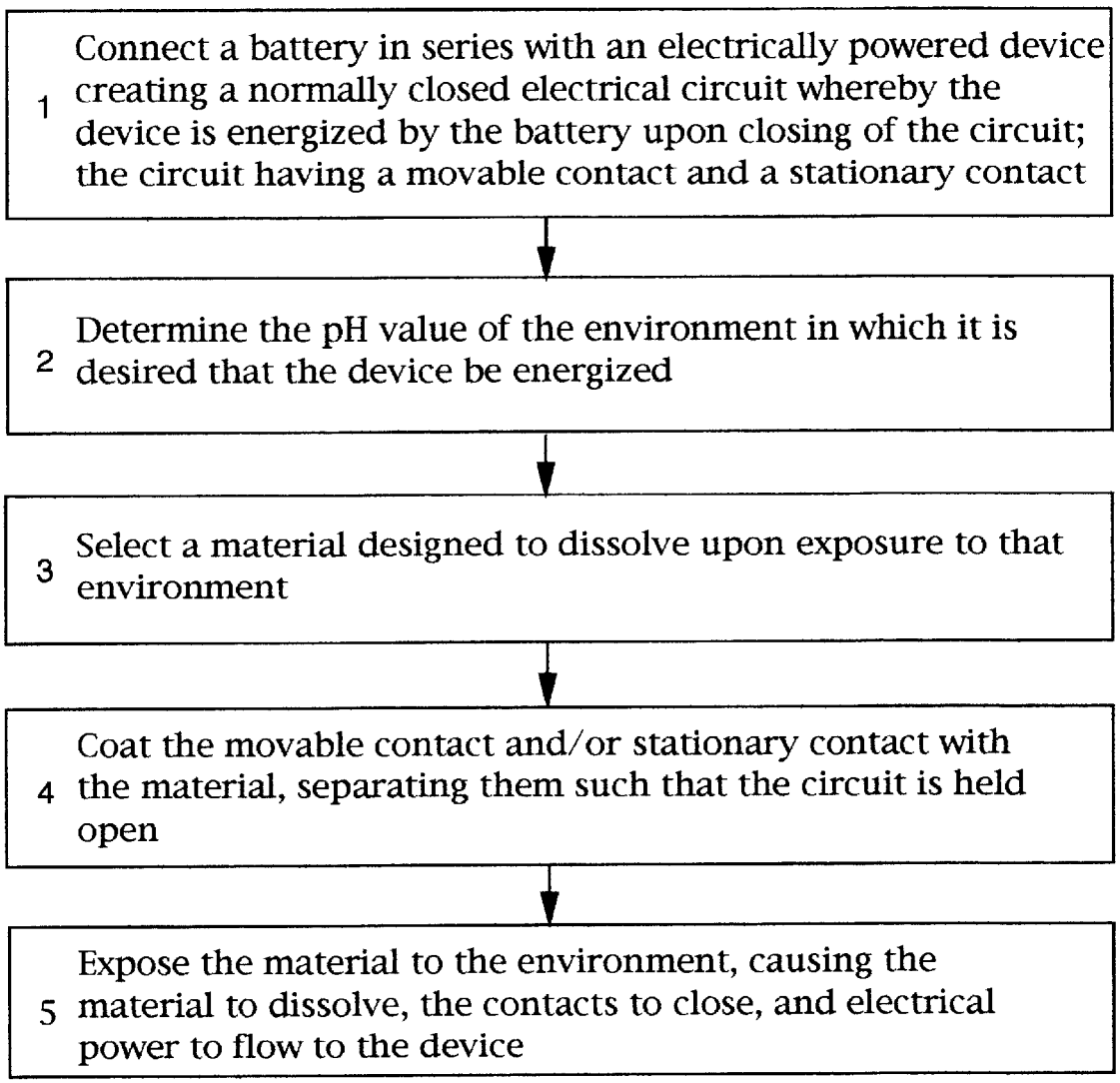

SYSTEM AND METHOD TO DELAY CLOSURE OF A NORMALLY CLOSED ELECTRICAL CIRCUIT

BACKGROUND OF THE INVENTION

1. Field of Invention

This invention relates to delaying closure of an electrical circuit to delay activation of an electrically powered device until its activation is desired.

2. Prior Art

Colon cancer is the second leading cause of death in humans. It is curable if it is detected early. The current method of choice for early detection of colon cancer is a colonoscopy. Unfortunately, for many, colonoscopy is an expensive and uncomfortable procedure. Also, there is a risk that the colon will be punctured during the procedure. Consequently, many people opt not to have or postpone having the procedure. As a result, thousands of people die every year because they do not get a colonoscopy.

A less intrusive and cheaper method for early detection of cancer has been developed. It is described in U.S. Pat. No. 5,604,531 to Iddan, et al., Feb. 18, 1997 In this method, a small endoscopic capsule is swallowed. The capsule contains, inter alia, a means for illumination, a video camera, a lens arrangement and a transmitter. The capsule travels through the body, taking pictures along the alimentary canal and transmitting them to a receiver attached to a belt worn by the patient. Patients are permitted to move around normally during the approximate 8 hour procedure. Since the device must be small enough to be swallowed, the size of its power source, a battery, and the amount of power it can provide are severely limited. Further, the capsule must be turned on before it is swallowed. Therefore, the principal disadvantage of this device is that the power source is depleted before it completes an investigation of the small intestine and colon. Consequently, the device is unable to investigate for cancer and other abnormalities in these parts of the body. My invention solves this problem by delaying activation of devices, such as this capsule, until needed.

There are several patents covering methods used to delay activation of electrically powered devices until they are needed. U.S. Pat. No. 5,057,824 to Stokes, Jul. 30, 1990 uses a normally closed switch held open by a removable spacer. It is designed to be used in security systems to conserve battery power until the device is ready for use. Upon manual removal of the spacer the switch closes and power is supplied. The principle disadvantage of this method is that it must be activated manually, and thus cannot be activated while in an environment that is not directly accessible, such as the human alimentary canal. If the removable spacer method were used to delay activation of the endoscopic capsule in U.S. Pat. No. 5,604,531, it would need to be activated prior to being swallowed; accordingly, the device would still run out of power prior to completing an investigation of the small intestine and colon.

U.S. Pat. No. 4,278,077 to Mizumoto, Jul. 14, 1981 uses an induction system to energize an electromagnetic field in a coil around a permanent magnet located in the device. This method energizes the device when it is needed. The principal disadvantage of this device is that it requires the patient to remain in a stationary position during the entire 8 hour process. Furthermore, this method cannot be used to energize the endoscopic capsule in U.S. Pat. No. 5,604,531 to Iddan, et al., Feb. 18, 1997 due to size constraints.

SUMMARY OF THE INVENTION

The present invention is a system and method to delay closure of an electrical circuit of a battery-powered electrical device, intended to operate remotely in an environment in which the pH value changes from one value to another. More specifically, two electrical contacts, at least one being movable, of a normally closed electrical circuit, connecting a battery in series with a battery-powered electrical device, are separated by a material that holds the circuit open until the device is exposed to an environment having a specified pH value. Exposure of the material to an environment having that specified pH value causes the material to dissolve. The dissolving of the material causes the circuit to close, energizing the device.

Accordingly, several objects and advantages of my invention are to provide a means to delay activation of a battery-powered device by holding it in a deactivated condition until ready for use. Another object is to provide a means by which an electrical device can be self-activated at a specific point within an environment that is difficult to access, such as the human alimentary canal.

Another object is to use the pH value of an environment to dissolve a pH-sensitive material separating electrical contacts to dissolve the material and activate a battery-powered electrical device.

Further objects and advantages of my invention will become apparent from review of the process flow chart, drawings and description of a preferred embodiment.

BRIEF DESCRIPTION OF THE DRAWINGS

The present invention will be understood more fully from the following description taken in conjunction with the drawings in which:

FIG. 4 is a process flow chart for the present invention.

DETAILED DESCRIPTION OF THE PREFERRED EMBODIMENT

This invention is primarily intended for use with a swallowable endoscopic capsule, as described in U.S. Pat. No. 5,604,531 to Iddan, et al., Feb. 18, 1997 The endoscopic capsule is designed to take pictures of the human alimentary canal. The capsule includes a camera system, an optical system, and a transmitter and is battery powered. The capsule travels through the alimentary canal from the mouth to the stomach, small intestine and colon. Due to size constraints and the fact that its battery must be activated before it is swallowed, the device runs out of battery power before reaching the colon. My invention allows the device to be activated just prior to reaching the small intestine and colon so that it has enough battery power to remain active while traveling through the small intestine and the colon.

Figure 1:
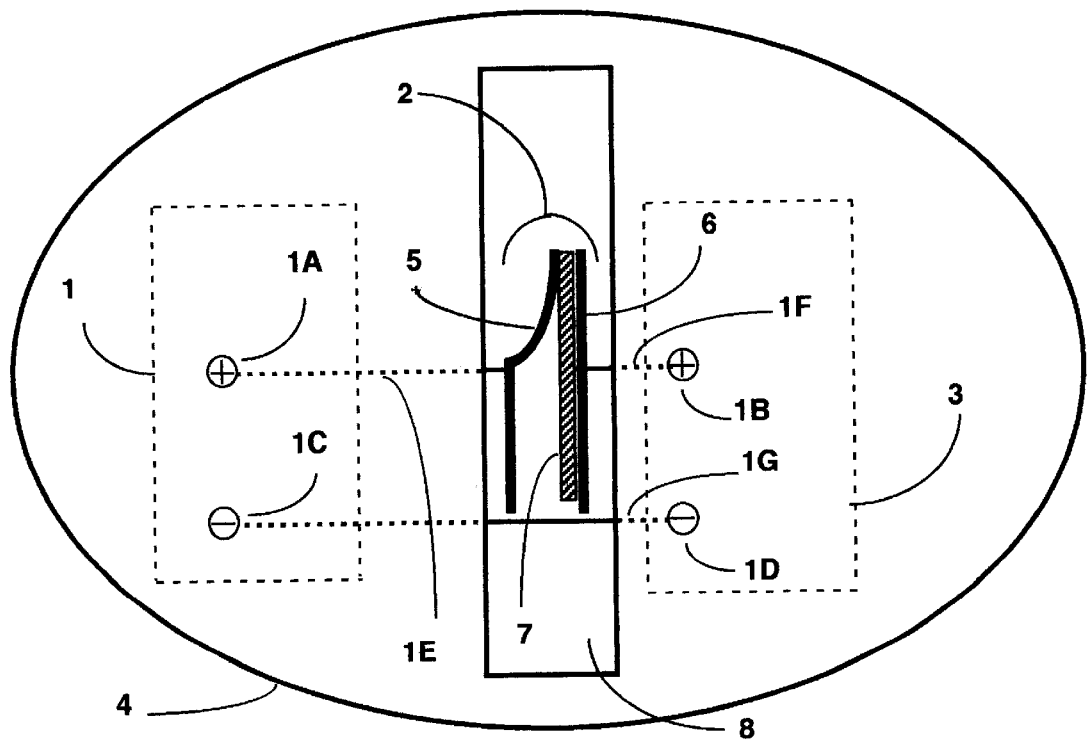
FIG. 1 shows the normally closed switch, according to the present invention, held open by a pH-sensitive material and connected in series between the battery and electrical circuitry of a swallowable endoscopic capsule.

FIG. 1 shows the preferred embodiment having a normally closed switch held open by a pH-sensitive material and connected in series between the battery and electrical circuitry of a swallowable endoscopic capsule. The normally closed switch 2 has a movable contact 5 and a stationary contact 6. Pursuant to the preferred embodiment of my invention, the stationary contact 6 is coated with a pH-sensitive material 7 designed to dissolve when exposed to an environment having a specified pH value. The material 7 holds the movable contact 5 separate from the stationary contact 6, keeping the battery 1 and battery-powered electrical device 3 inactive. The preferred material 7 is made by Colorcon Company of West Point, Pa. 19486, described in U.S. Pat. No. 5,811,121 to Wu, et al., Sep. 22, 1998 and is under the trademark name of SURETERIC. Color may be added to the material 7 to allow for easy identification of differing pH values. The movable contact 5 and stationary contact 6 may be made of various materials, including, but not limited to, brass, copper and phosphor bronze.

Pursuant to my invention, and as shown in FIG. 1, the protective covering 4 of the endoscopic capsule contains an opening 8, allowing the material 7 coated on the stationary contact 6 to be exposed directly to the various environments of the alimentary canal as the capsule travels from the mouth through the stomach, small intestine and colon. Each environment through which the capsule travels has an ever-increasing pH value, starting with a value of 1–2 in the stomach and finally reaching a value above 7 in the colon. The material 7 that holds the switch 2 open will dissolve upon reaching an environment in which the pH value is greater than that of the material 7. For example, if the stationary contact 6 is coated with a material with a pH of 4, it will dissolve after leaving the stomach and before reaching the colon. Once the material 7 is dissolved, the switch 2 will close, causing the battery 1 to provide power to electrically powered device 3.

FIG. 1 shows a battery 1 inside of a protective cover 4, which contains an opening 8. Positive electrode 1A of battery 1 is connected to movable contact 5 of a normally closed switch 2 by wire 1E, and stationary contact 6 of switch 2 is connected to the positive lead 1B of electrically powered device 3 by wire 1F. Negative electrode 1C of battery 1 is connected to the negative lead 1D of 3 by wire 1G.

Figure 2:
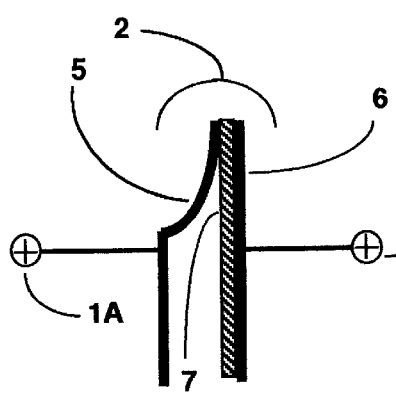
FIG. 2 shows the normally closed switch, according to the present invention, held open by the pH-sensitive material separating the contacts; A system and method are provided to delay closure of an electrical circuit of a battery-powered electrical device, intended to operate remotely in an environment in which the pH value changes from one value to another. More specifically, two electrical contacts, at least one being movable, of a normally closed electrical circuit, connecting a battery in series with a battery-powered electrical device, are separated by a material that holds the circuit open until the device is exposed to an environment having a specified pH value. Exposure of the material to an environment having that specified pH value causes the material to dissolve. The dissolving of the material causes the circuit to close, energizing the device.

As shown in FIG. 2, a normally closed switch 2 with movable contact 5 is held apart from stationary contact 6 by material 7 that is designed to dissolve at a specified pH value. The material 7 prevents electrical current from flowing from positive electrode 1A to positive lead 1B.

Figure 3:
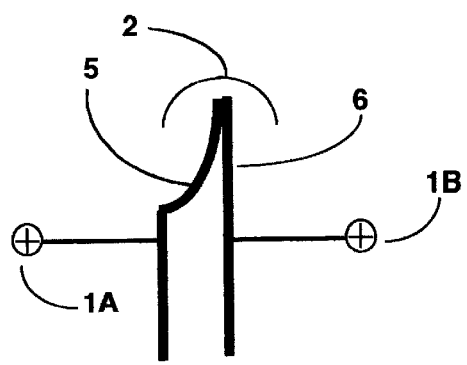
FIG. 3 shows the normally closed switch, according to the present invention, after the pH-sensitive material has dissolved.

FIG. 3 shows a normally closed switch 2 after the material 7, shown in FIG. 2, dissolves. Accordingly, FIG. 3 shows a normally closed switch 2 with movable contact 5 closed against stationary contact 6, allowing current to flow from positive electrode 1A to positive lead 1B.

FIG. 4 is a process flow chart for the preferred embodiment of the present invention. At step 1, a battery is connected in series with an electrically powered device, creating a normally closed electrical circuit whereby the device is energized by the battery upon closing of the circuit. The circuit has a movable contact and stationary contact. At step 2, the pH value of the environment in which it is desired that the device be energized is determined. At step 3, a material designed to dissolve upon exposure to that environment is selected. At step 4, either the movable contact and/or stationary contact is coated with the material, separating them such that the circuit is held open. Finally, at step 5, the material is exposed to the desired environment, causing the material to dissolve, the contacts to close, and electrical power to flow to the device.

As an alternative embodiment, the pH-sensitive material is applied directly to the positive and/or negative ends of at least one battery within the circuit. The material holds the circuit open until the material dissolves. When the material dissolves, a movable contact holding the battery in place closes against the battery, allowing current to flow.

From the above, it should be understood that the embodiments described, in regard to the drawings, are merely exemplary and that a person skilled in the art may make variations and modifications to the shown embodiments without departing from the spirit and scope of the invention. All such variations and modifications are intended to be included within the scope of the invention as defined by the appended claims. This information is meant to be illustrative and not limiting.

I claim:

1. A system for delaying activation of a battery-powered electrical device intended to operate remotely in an environment in which a pH value changes from a first value to a second value comprising:

(a) a normally closed electrical circuit; said circuit having a battery connected in series with an electrically powered device, whereby said electrically powered device is energized by said battery upon closing of said circuit;

(b) said circuit having a first electrical contact means and a second electrical contact means; said first electrical contact means being a movable contact located on said battery or said electrically powered device or between said battery and said electrically powered device; said second electrical contact means being located on said battery or said electrically powered device or between said battery and said electrically powered device; and (c) an electrically insulating separating member disposed between and separating said first electrical contact means from said second electrical contact means, holding said circuit open; said separating member dissolvable upon exposure to an environment in which the pH value is equal to said second value.

2. A system as claimed in claim 1 in which said first value and said second value are between 1 and 14, inclusive.

3. A system as claimed in claim 1 in which the dissolving of said separating member material causes said first electrical contact to close against said second electrical contact, energizing said electrically powered device.

4. A method for delaying activation of a battery-powered electrical device intended to operate remotely in an environment in which a pH value changes from a first value to a second value at which it is desirable to activate said device, comprising the steps of:

(a) connecting a battery in series with an electrically powered device, creating a normally closed electrical circuit whereby said electrical device is energized by said battery upon closing of said circuit; said circuit having a first electrical contact means and a second electrical contact means; said first electrical contact means being a movable contact located on said battery or said electrically powered device or between said battery and said electrically powered device; said second electrical contact means being located on said battery or said electrically powered device or between said battery and said electrically powered device;

(b) determining the pH value of the environment in which it is desired that the electrically powered device be energized;

(c) selecting an electrically insulating material which is dissolvable Signed to dissolve upon exposure to said environment;

(d) separating said first electrical contact from said second electrical contact with a separating member fabricated of said material, such that said circuit is held open; and (e) exposing said separating member to the environment in which the pH value is equal to said second value.

5. The method of claim 4 wherein said separating member dissolves upon exposure to the environment in which the pH value is equal to said second value.

6. The method of claim 4 wherein the dissolving of said separating member causes said first electrical contact means to close against said second electrical contact means, energizing said electrically powered device.

* * * * *

UNITED STATES PATENT AND TRADEMARK OFFICE
CERTIFICATE OF CORRECTION

PATENT NO.   : 6,635,834 B1
DATED        : October 21, 2003
INVENTOR(S)  : Justin Bernard Wenner It is certified that error appears in the above-identified patent and that said Letters Patent is hereby corrected as shown below:

Column 5,
Line 12, delete "Signed to dissolve"

Signed and Sealed this

Sixteenth Day of March, 2004

JON W. DUDAS
*Acting Director of the United States Patent and Trademark Office*